US010481373B2

(12) United States Patent
Lee et al.

(10) Patent No.: US 10,481,373 B2
(45) Date of Patent: Nov. 19, 2019

(54) SURGICAL OPTICAL ZOOM SYSTEM

(71) Applicants: Tammy Kee-Wai Lee, Toronto (CA); William La, Toronto (CA); Paul Quevedo, Toronto (CA); Aryeh Benjamin Taub, Toronto (CA); Yusuf Bismilla, Toronto (CA); Sam Anthony Leitch, Toronto (CA); Yuri Alexander Kuzyk, Toronto (CA); Ze Shan Yao, Toronto (CA); Michael Frank Gunter Wood, Toronto (CA)

(72) Inventors: Tammy Kee-Wai Lee, Toronto (CA); William La, Toronto (CA); Paul Quevedo, Toronto (CA); Aryeh Benjamin Taub, Toronto (CA); Yusuf Bismilla, Toronto (CA); Sam Anthony Leitch, Toronto (CA); Yuri Alexander Kuzyk, Toronto (CA); Ze Shan Yao, Toronto (CA); Michael Frank Gunter Wood, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 0 days.

(21) Appl. No.: 16/152,264

(22) Filed: Oct. 4, 2018

(65) Prior Publication Data
US 2019/0107700 A1  Apr. 11, 2019

(30) Foreign Application Priority Data
Oct. 6, 2017 (CA) .................... 2981726

(51) Int. Cl.
G02B 21/00 (2006.01)
G02B 21/36 (2006.01)
A61B 90/20 (2016.01)
G02B 21/02 (2006.01)
G02B 21/24 (2006.01)
(Continued)

(52) U.S. Cl.
CPC .......... G02B 21/0012 (2013.01); A61B 90/20 (2016.02); G02B 21/025 (2013.01); G02B 21/245 (2013.01); G02B 21/36 (2013.01); G02B 21/365 (2013.01); G02B 21/362 (2013.01); G06T 7/246 (2017.01); G06T 7/73 (2017.01); G06T 2207/30204 (2013.01); G06T 2207/30244 (2013.01); H04N 5/2254 (2013.01)

(58) Field of Classification Search
CPC .... G02B 21/0012; G02B 21/36; A61B 90/20; G06T 2207/30204; G06T 2207/30244; G06T 7/246; G06T 7/73
See application file for complete search history.

(56) References Cited

U.S. PATENT DOCUMENTS 9,397,587 B2 * 7/2016 Youcef-Toumi ....... G01Q 30/04
2006/0187562 A1 * 8/2006 Mounnarat ............ G02B 7/102
359/824
(Continued)

Primary Examiner — Dramos Kalapodas
(74) Attorney, Agent, or Firm — Ridout & Maybee LLP

(57) ABSTRACT

Methods and systems for controlling a surgical microscope. Moveable optics of the surgical microscope are controlled using two sets of control parameters, to reduce jitter and image instability. Shifts in the image due to changes in temperature or due to the use of optical filter can also be compensated. Misalignment between the mechanical axis and the optical axis of the surgical microscope can also be corrected.

11 Claims, 17 Drawing Sheets

(51) Int. Cl.
 *G06T 7/246* (2017.01)
 *G06T 7/73* (2017.01)
 *H04N 5/225* (2006.01)

(56) References Cited

U.S. PATENT DOCUMENTS

| | | | |
|---|---|---|---|
| 2007/0200947 A1* | 8/2007 | Kobaru | H01J 37/21 348/345 |
| 2009/0147340 A1* | 6/2009 | Lipton | G02B 7/08 359/230 |
| 2009/0310229 A1* | 12/2009 | Yang | A61B 1/00096 359/694 |
| 2012/0075519 A1* | 3/2012 | Blasch | G02B 7/102 348/340 |
| 2012/0309636 A1* | 12/2012 | Gibbons | B01L 3/0275 506/9 |
| 2014/0104618 A1* | 4/2014 | Potsaid | G02B 26/105 356/497 |
| 2014/0226003 A1* | 8/2014 | Phaneuf | H01J 37/222 348/80 |
| 2016/0113728 A1* | 4/2016 | Piron | A61B 17/3421 606/130 |
| 2017/0017058 A1* | 1/2017 | Sumioka | G02B 7/09 |

* cited by examiner

SURGICAL OPTICAL ZOOM SYSTEM

CROSS-REFERENCE TO RELATED APPLICATIONS

The present disclosure claims priority from Canadian Patent Application no. 2,981,726, filed Oct. 6, 2017, entitled "SURGICAL OPTICAL ZOOM SYSTEM", the entirety of which is hereby incorporated by reference.

FIELD

The present disclosure is generally related to optical imaging systems, including optical imaging systems suitable for use in image guided medical procedures, and for medical procedures requiring high optical zoom.

BACKGROUND

Surgical microscopes are often used during surgical procedures to provide a detailed or magnified view of the surgical site. Often, a high optical zoom is required while maintaining a large stand-off distance. Conventional surgical microscopes may exhibit noticeable image jitter at high zoom, which is undesirable. Further, insufficient holding force for the optical carriage may result in an unstable image.

As well, minor misalignment between the mechanical axis and optical axis of the imaging system, which may otherwise be acceptable or negligible at lower zoom levels, may cause positioning errors at high zoom levels.

SUMMARY

In some aspects, there is provided a surgical microscope for capturing an image of a target during a surgical procedure. The surgical microscope includes an optical assembly including at least one moveable optics, and an actuator for positioning the moveable optics. The actuator includes a pulley system for moving the optics along a set of rails. The surgical microscope also includes a sensor for detecting the position of the moveable optics, a controller for controlling the actuator in response to received control input, and a camera for capturing the image of the target from the optical assembly. The controller is configured to receive control input indicating a target position for the moveable optics. The controller is also configured to control the actuator to position the moveable optics towards the target position. The actuator is controlled according to a first set of control parameters. The controller is also configured to, upon receiving signals from the sensor indicating that the moveable optics is within a threshold range of the target position, switch to a second set of control parameters for controlling the actuator. The controller is also configured to control the actuator to maintain the moveable optics at the target position at steady state.

In some examples, the surgical microscope may include a filter wheel that is positionable by a filter wheel actuator to position a selectable optical filter in an optical path of the optics.

In some examples, use of the selectable optical filter may cause a shift in the optical path. The controller may be further configured to determine a compensation amount to adjust the target position for the moveable optics, to compensate for the shift, and to adjust the target position accordingly.

In some examples, the surgical microscope may include a temperature sensor. The controller may be further configured to determine a compensation amount to adjust the target position for the moveable optics, to compensate for temperature-dependent shift in an optical path of the optics, and to adjust the target position accordingly.

In some aspects, there is provided a method for controlling a surgical microscope. The method includes receiving control input indicating a target position for a moveable optics of the surgical microscope. The method also includes controlling an actuator of the moveable optics to position the moveable optics towards the target position. The actuator is controlled according to a first set of control parameters. The actuator includes a pulley system for moving the optics along a set of rails. The method also includes, upon receiving signals from a position sensor indicating that the moveable optics is within a threshold range of the target position, switching to a second set of control parameters for controlling the actuator. The method also includes controlling the actuator to maintain the moveable optics at the target position at steady state.

In some examples, when an optical filter is positioned in an optical path of the optics, the method may include determining a compensation amount to adjust the target position for the moveable optics, to compensate for a shift in the optical path caused by the optical filter, and adjusting the target position accordingly.

In some examples, the method may include receiving information from a temperature sensor indicating a surrounding temperature of the optics. The method may further include determining a compensation amount to adjust the target position for the moveable optics, to compensate for a temperature-dependent shift in an optical path of the optics, and adjusting the target position accordingly.

In some aspects, there is provided a method of correcting for misalignment between a mechanical axis of a surgical microscope and an optical axis of the surgical microscope. The mechanical axis is defined by a housing of the surgical microscope and the optical axis is defined by an optical assembly of the surgical microscope. The method includes receiving control input to move the surgical microscope to a target working distance from a target. The method also includes applying a correction matrix to transform the target working distance from an optical axis frame of reference to a mechanical axis frame of reference. The correction matrix contains correction terms to correct for misalignment between the optical axis and the mechanical axis. The method also includes moving the surgical microscope according to the transformed working distance.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
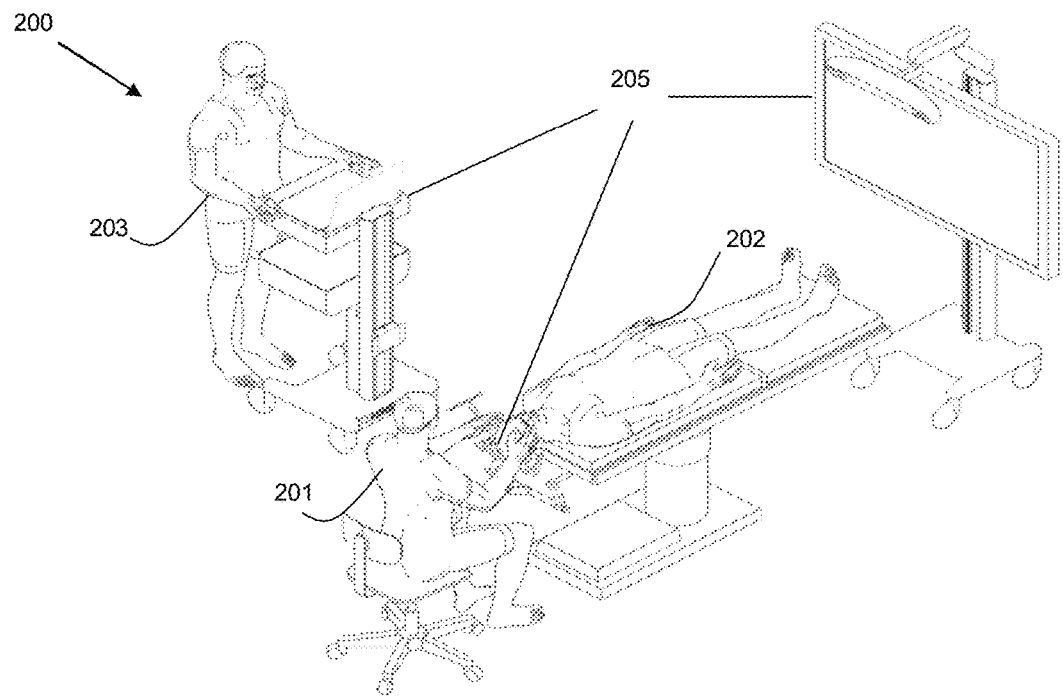
FIG. 1 shows an example navigation system to support image guided surgery.

The systems and methods described herein may be useful in the field of neurosurgery, including oncological care, neurodegenerative disease, stroke, brain trauma and orthopedic surgery. The teachings of the present disclosure may be applicable to other conditions or fields of medicine. It should be noted that while the present disclosure describes examples in the context of neurosurgery, the present disclosure may be applicable to other surgical procedures that may use intraoperative optical imaging.

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not part of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" may be understood to mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port. The present disclosure applies equally well to other medical procedures performed on other parts of the body, as well as to medical procedures that do not use an access port. Various examples of the present disclosure may be generally suitable for use in any medical procedure that may use optical imaging systems, for example any medical procedure that may benefit from having intraoperative imaging at high zoom level.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon performing the procedure has the best possible view of the surgical site of interest at a sufficiently high zoom level, with a stable and clear image. At the same time, the imaging system should maintain a sufficient stand-off distance from the site of interest, to avoid contamination and also to avoid obstructing the surgeon.

In FIG. 1, an exemplary navigation system environment 200 is shown, which may be used to support navigated image-guided surgery. As shown in FIG. 1, surgeon 201 conducts a surgery on a patient 202 in an operating room (OR) environment. A medical navigation system 205 may include an equipment tower, tracking system, displays and tracked instruments to assist the surgeon 201 during his procedure. An operator 203 may also be present to operate, control and provide assistance for the medical navigation system 205.

Figure 2:
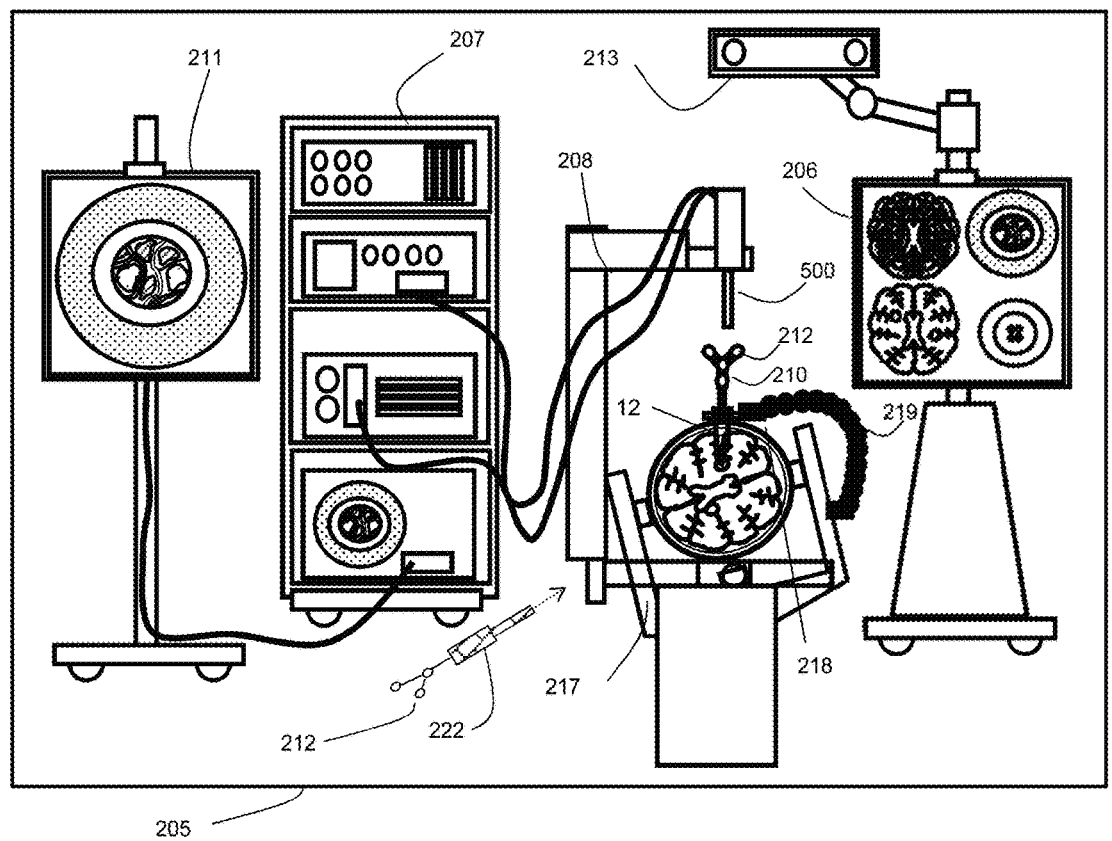
FIG. 2 is a diagram illustrating system components of an example navigation system.

FIG. 2 shows a diagram illustrating an example medical navigation system 205 in greater detail. The disclosed optical imaging system may be used in the context of the medical navigation system 205. The medical navigation system 205 may include one or more displays 206, 211 for displaying a video image, an equipment tower 207, and a positioning system 208, such as a mechanical arm, which may support an optical imaging system 500 (which may include an optical scope). One or more of the displays a, 211 may include a touch-sensitive display for receiving touch input. The equipment tower 207 may be mounted on a frame (e.g., a rack or cart) and may contain a power supply and a computer or controller that may execute planning software, navigation software and/or other software to manage the positioning system 208 and/or one or more instruments tracked by the navigation system 205. In some examples, the equipment tower 207 may be a single tower configuration operating with dual displays 206, 211, however other configurations may also exist (e.g., dual tower, single display, etc.). Furthermore, the equipment tower 207 may also be configured with a universal power supply (UPS) to provide for emergency power, in addition to a regular AC adapter power supply.

A portion of the patient's anatomy may be held in place by a holder. For example, as shown the patient's head and brain may be held in place by a head holder 217. An access port 12 and associated introducer 210 may be inserted into the head, to provide access to a surgical site in the head. The imaging system 500 may be used to view down the access port 12 at a sufficient magnification to allow for enhanced visibility down the access port 12. The output of the imaging system 500 may be received by one or more computers or controllers to generate a view that may be depicted on a visual display (e.g., one or more displays 206, 211).

In some examples, the navigation system 205 may include a tracked pointer 222. The tracked pointer 222, which may include markers 212 to enable tracking by a tracking camera 213, may be used to identify points (e.g., fiducial points) on a patient. An operator, typically a nurse or the surgeon 201, may use the tracked pointer 222 to identify the location of points on the patient 202, in order to register the location of selected points on the patient 202 in the navigation system 205. It should be noted that a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Tracking markers 212 may be connected to the introducer 210 for tracking by the tracking camera 213, which may provide positional information of the introducer 210 from the navigation system 205. In some examples, the tracking markers 212 may be alternatively or additionally attached to the access port 12. In some examples, the tracking camera 213 may be a 3D infrared optical tracking stereo camera similar to one made by Northern Digital Imaging (NDI). In some examples, the tracking camera 213 may be instead an electromagnetic system (not shown), such as a field transmitter that may use one or more receiver coils located on the tool(s) to be tracked. A known profile of the electromagnetic field and known position of receiver coil(s) relative to each other may be used to infer the location of the tracked tool(s) using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference. Location data of the positioning system 208 and/or access port 12 may be determined by the tracking camera 213 by detection of the tracking markers 212 placed on or otherwise in fixed relation (e.g., in rigid connection) to any of the positioning system 208, the access port 12, the introducer 210, the tracked pointer 222 and/or other tracked instruments. The tracking marker(s) 212 may be active or passive markers. A display 206, 211 may provide an output of the computed data of the navigation system 205. In some examples, the output provided by the display 206, 211 may include axial, sagittal and coronal views of patient anatomy as part of a multi-view output.

The active or passive tracking markers 212 may be placed on tools (e.g., the access port 12 and/or the imaging system 500) to be tracked, to determine the location and orientation of these tools using the tracking camera 213 and navigation system 205. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3D of a tracked tool in a virtual space. The position and orientation of the tracked tool in 3D may be tracked in six degrees of freedom (e.g., x, y, z coordinates and pitch, yaw, roll rotations), in five degrees of freedom (e.g., x, y, z, coordinate and two degrees of free rotation), but preferably tracked in at least three degrees of freedom (e.g., tracking the position of the tip of a tool in at least x, y, z coordinates). In typical use with navigation systems, at least three markers 212 are provided on a tracked tool to define the tool in virtual space, however it is known to be advantageous for four or more markers 212 to be used.

Camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. An example of such an apparatus may be tracking devices such as the Polaris® system available from Northern Digital Inc. In some examples, the spatial position and orientation of the tracked tool and/or the actual and desired position and orientation of the positioning system 208 may be determined by optical detection using a camera. The optical detection may be done using an optical camera, rendering the markers 212 optically visible.

In some examples, the markers 212 (e.g., reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 205. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 205. The markers 212 may be tracked relative to a reference point or reference object in the operating room, such as the patient 202.

Various types of markers may be used. The markers 212 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from a tracking camera to the markers 212, and using an optical tracking system may avoid additional noise from electrical emission and detection systems.

In some examples, the markers 212 may include printed or 3D designs that may be used for detection by an auxiliary camera, such as a wide-field camera (not shown) and/or the imaging system 500. Printed markers may also be used as a calibration pattern, for example to provide distance information (e.g., 3D distance information) to an optical detector. Printed identification markers may include designs such as concentric circles with different ring spacing and/or different types of bar codes, among other designs. In some examples, in addition to or in place of using markers 212, the contours of known objects (e.g., the side of the access port 12) could be captured by and identified using optical imaging devices and the tracking system.

A guide clamp 218 (or more generally a guide) for holding the access port 12 may be provided. The guide clamp 218 may allow the access port 12 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

In a surgical operating room (or theatre), setup of a navigation system may be relatively complicated; there may be many pieces of equipment associated with the surgical procedure, as well as elements of the navigation system 205. Further, setup time typically increases as more equipment is added. To assist in addressing this, the navigation system 205 may include two additional wide-field cameras to enable video overlay information. Video overlay information can then be inserted into displayed images, such as images displayed on one or more of the displays 206, 211. The overlay information may illustrate the physical space where accuracy of the 3D tracking system (which is typically part of the navigation system) is greater, may illustrate the available range of motion of the positioning system 208 and/or the imaging system 500, and/or may help to guide head and/or patient positioning.

The navigation system 205 may provide tools to the neurosurgeon that may help to provide more relevant information to the surgeon, and may assist in improving performance and accuracy of port-based neurosurgical operations. Although described in the present disclosure in the context of port-based neurosurgery (e.g., for removal of brain tumors and/or for treatment of intracranial hemorrhages (ICH)), the navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 may be used for carrying out any or all of these procedures, with or without modification as appropriate.

For example, although the present disclosure may discuss the navigation system 205 in the context of neurosurgery, the same navigation system 205 may be used to carry out a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures may be conducted with or without a stereotactic frame. Both types of procedures may be performed using image-guidance. Frameless biopsies, in particular, may be conducted using the navigation system 205.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

Figure 3:
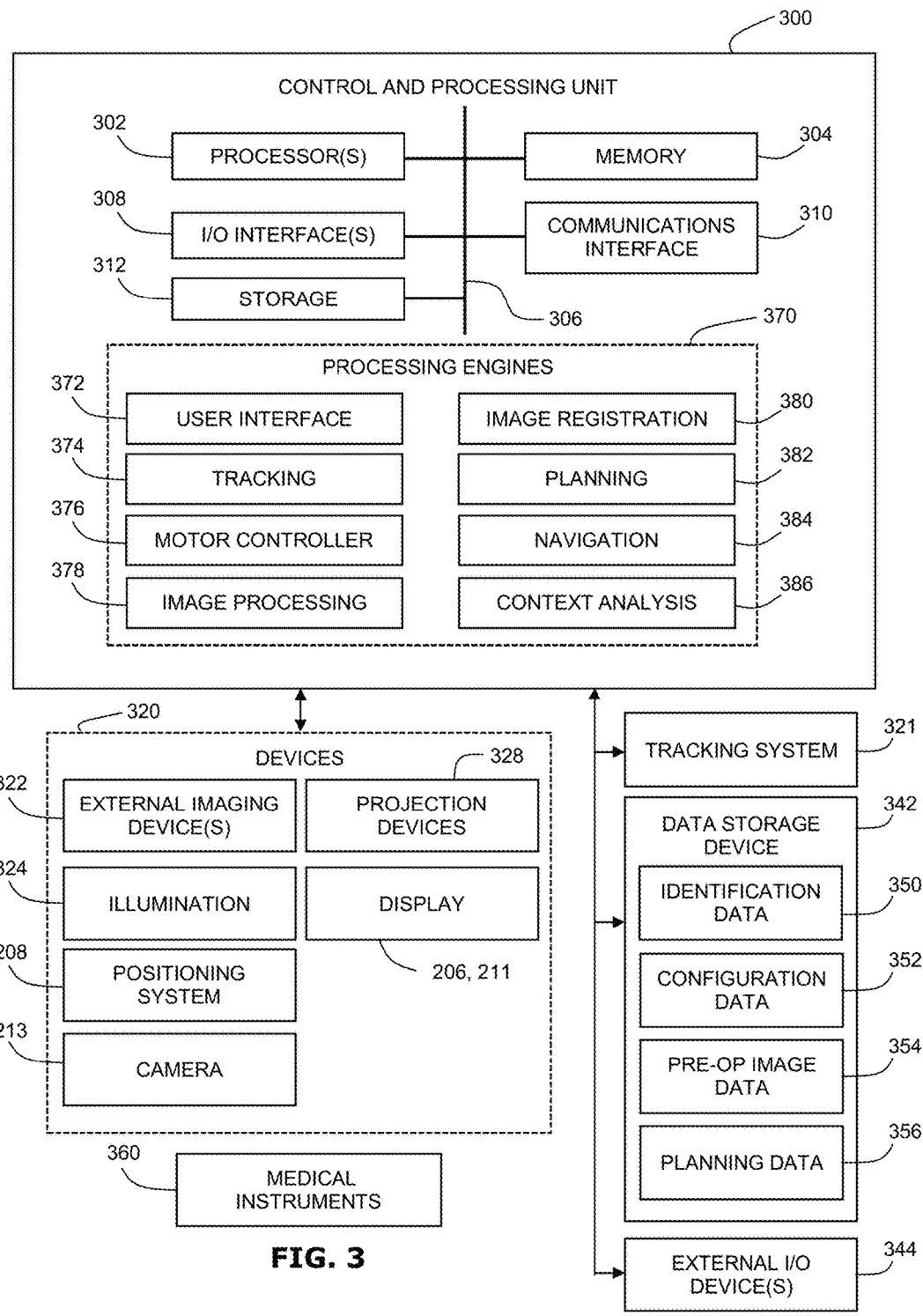
FIG. 3 is a block diagram illustrating an example control and processing system that may be used in the example navigation systems of FIGS. 1 and 2.

FIG. 3 is a block diagram illustrating a control and processing system 300 that may be used in the medical navigation system 205 shown in FIG. 2 (e.g., as part of the equipment tower 207). As shown in FIG. 3, in one example, control and processing system 300 may include one or more processors 302, a memory 304, a system bus 306, one or more input/output interfaces 308, a communications interface 310, and storage device 312. The control and processing system 300 may be interfaced with other external devices, such as a tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. The data storage device 342 may also include preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, the medical instruments 360 may include tracking markers such as tracking spheres that may be recognizable by the tracking camera 213. In one example, the tracking camera 213 may be an infrared (IR) tracking camera. In another example, as sheath placed over a medical instrument 360 may be connected to and controlled by the control and processing unit 300.

The control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, the positioning system 208, the tracking camera 213, one or more projection devices 328, and one or more displays 206, 211.

Exemplary aspects of the disclosure can be implemented via the processor(s) 302 and/or memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some examples the processing modules 370 may be stored in the memory 304 and the processing modules 370 may be collectively referred to as processing modules 370. In some examples, two or more modules 370 may be used together to perform a function. Although depicted as separate modules 370, the modules 370 may be embodied as a unified set of computer-readable instructions (e.g., stored in the memory 304) rather than distinct sets of instructions.

It is to be understood that the system is not intended to be limited to the components shown in FIG. 3. One or more components of the control and processing system 300 may be provided as an external component or device. In one example, the navigation module 384 may be provided as an external navigation system that is integrated with the control and processing system 300.

Some embodiments may be implemented using the processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

In some examples, the navigation system 205, which may include the control and processing unit 300, may provide tools to the surgeon that may help to improve the performance of the medical procedure and/or post-operative outcomes. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, examples of the present disclosure may be applied to any suitable medical procedure.

Figure 4A:
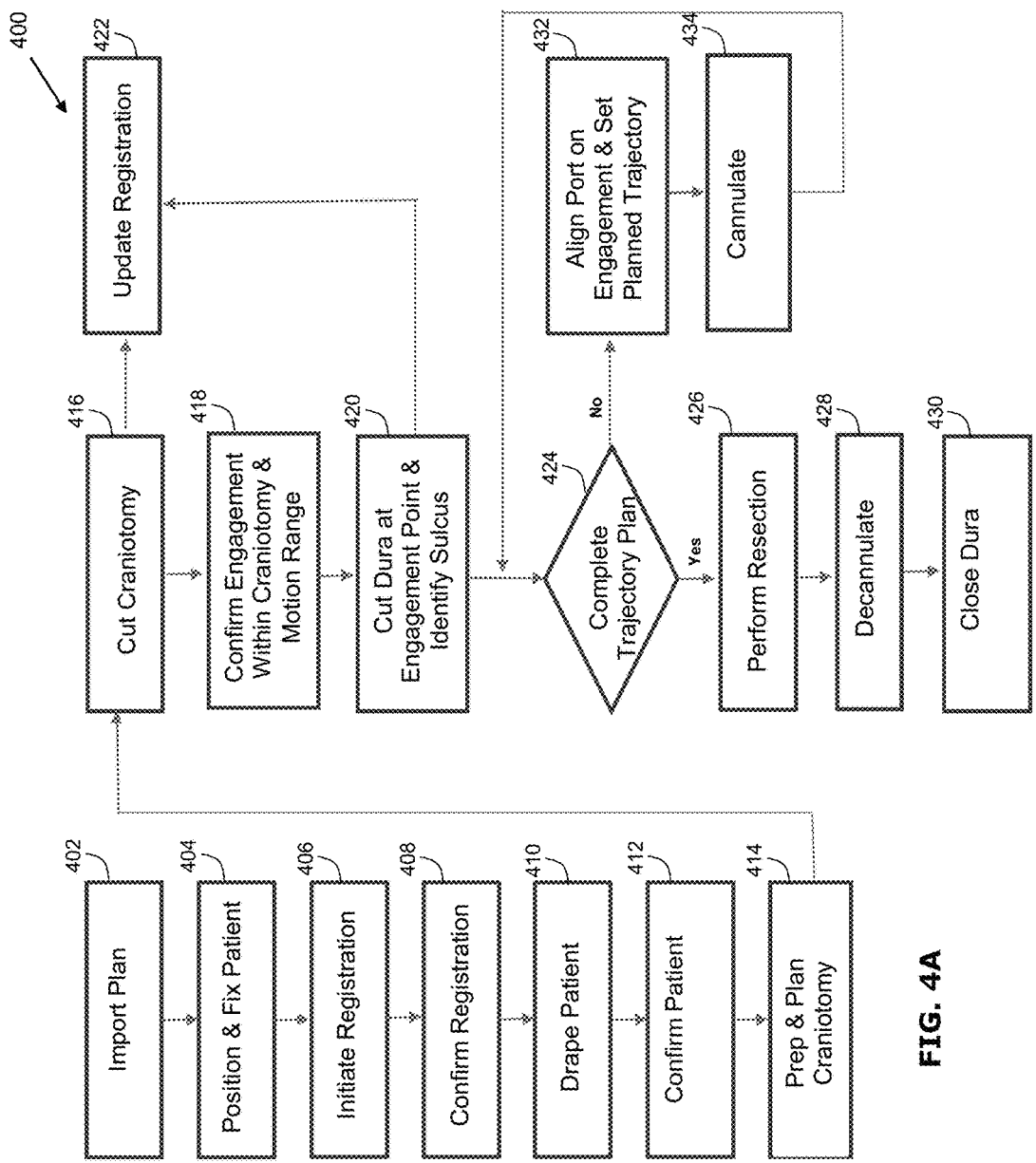
FIG. 4A is a flow chart illustrating an example method involved in a surgical procedure that may be implemented using the example navigation systems of FIGS. 1 and 2.

FIG. 4A is a flow chart illustrating an example method 400 of performing a port-based surgical procedure using a navigation system, such as the medical navigation system 205 described in relation to FIGS. 1 and 2. At a first block 402, the port-based surgical plan is imported.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower 207.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
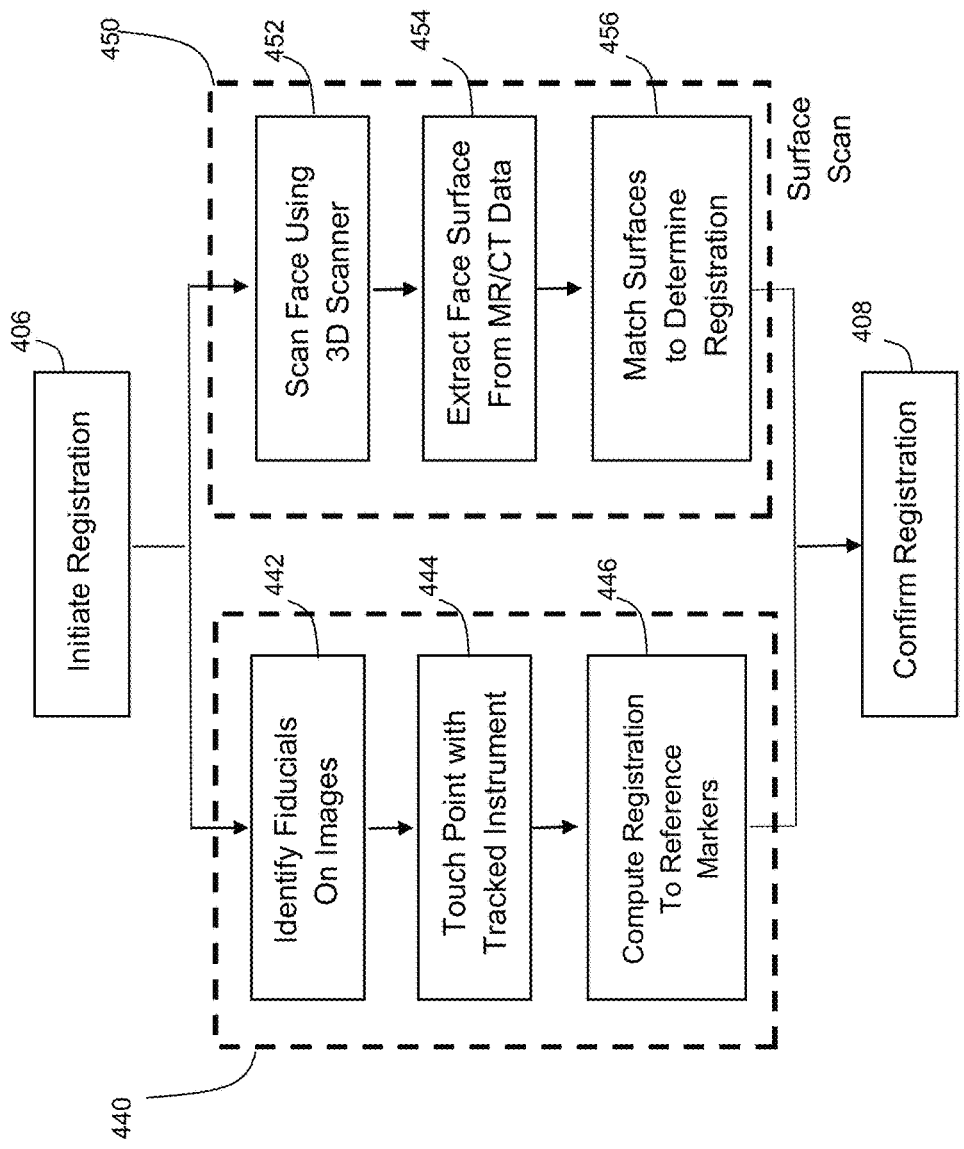
FIG. 4B is a flow chart illustrating an example method of registering a patient for a surgical procedure as outlined in FIG. 4A.

FIG. 4B is a flow chart illustrating an example method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 432, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 may acquire and maintain a reference of the location of the tools in use as well as the patient in three dimensional (3D) space. In other words, during a navigated neurosurgery, there may be a tracked reference frame that is fixed (e.g., relative to the patient's skull). During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
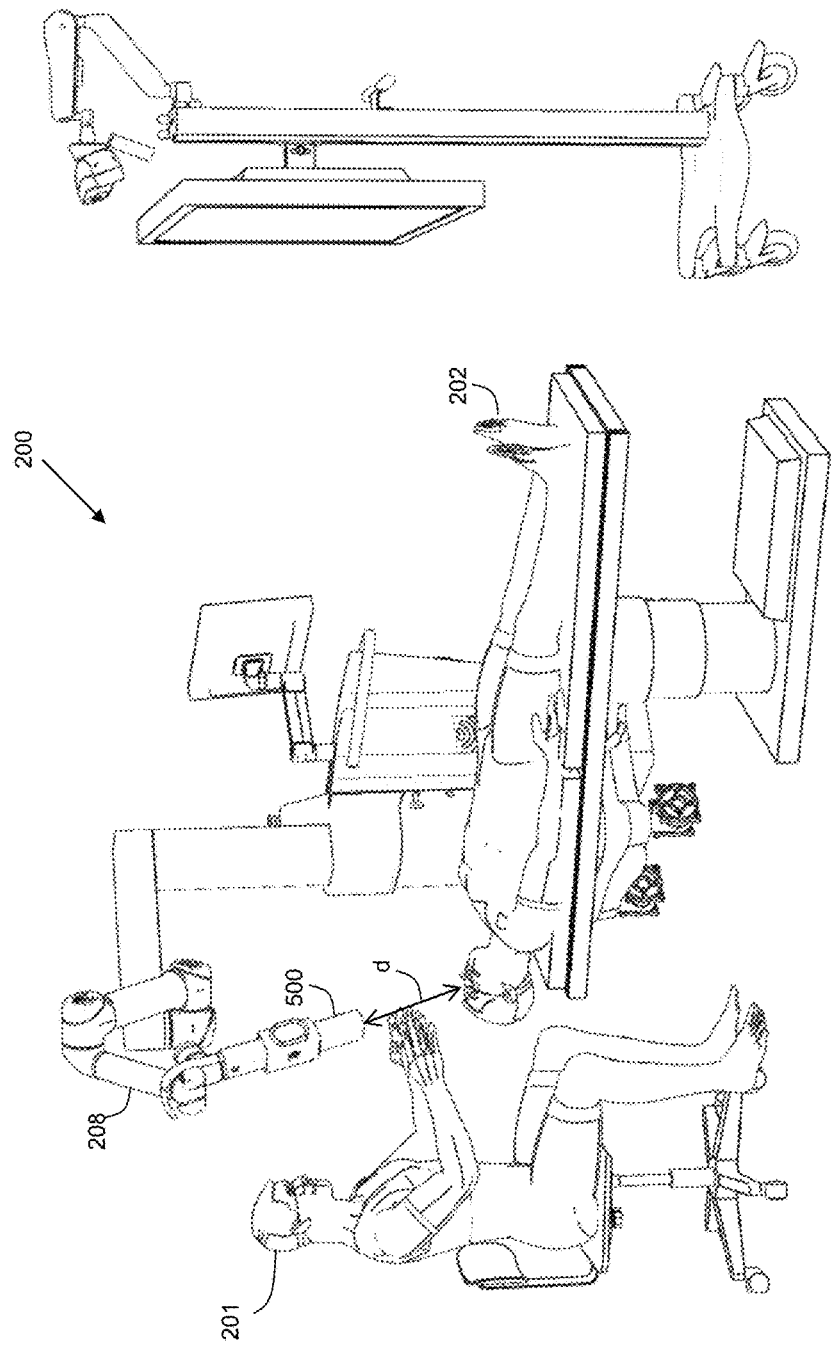
FIG. 5 shows the use of an example optical imaging system during a medical procedure.

FIG. 5 illustrates use of an example imaging system 500, described further below, in a medical procedure. Although FIG. 5 shows the imaging system 500 being used in the context of a navigation system environment 200 (e.g., using a navigation system as described above), the imaging system 500 may also be used outside of a navigation system environment (e.g., without any navigation support).

An operator, typically a surgeon 201, may use the imaging system 500 to observe the surgical site (e.g., to look down an access port). The imaging system 500 may be attached to a positioning system 208 (e.g., a controllable and adjustable robotic arm). The position and orientation of the positioning system 208, imaging system 500 and/or access port may be tracked using a tracking system, such as described for the navigation system 205. The distance d between the imaging system 500 (more specifically, the aperture of the imaging system 500) and the viewing target (e.g., the surface of the surgical site) may be referred to as the working distance. The imaging system 500 may be designed to be used in a predefined range of working distance (e.g., in the range of about 15 cm to about 75 cm). It should be noted that, if the imaging system 500 is mounted on the positioning system 208, the actual available range of working distance may be dependent on both the working distance of the imaging system 500 as well as the workspace and kinematics of the positioning system 208.

Figure 6:
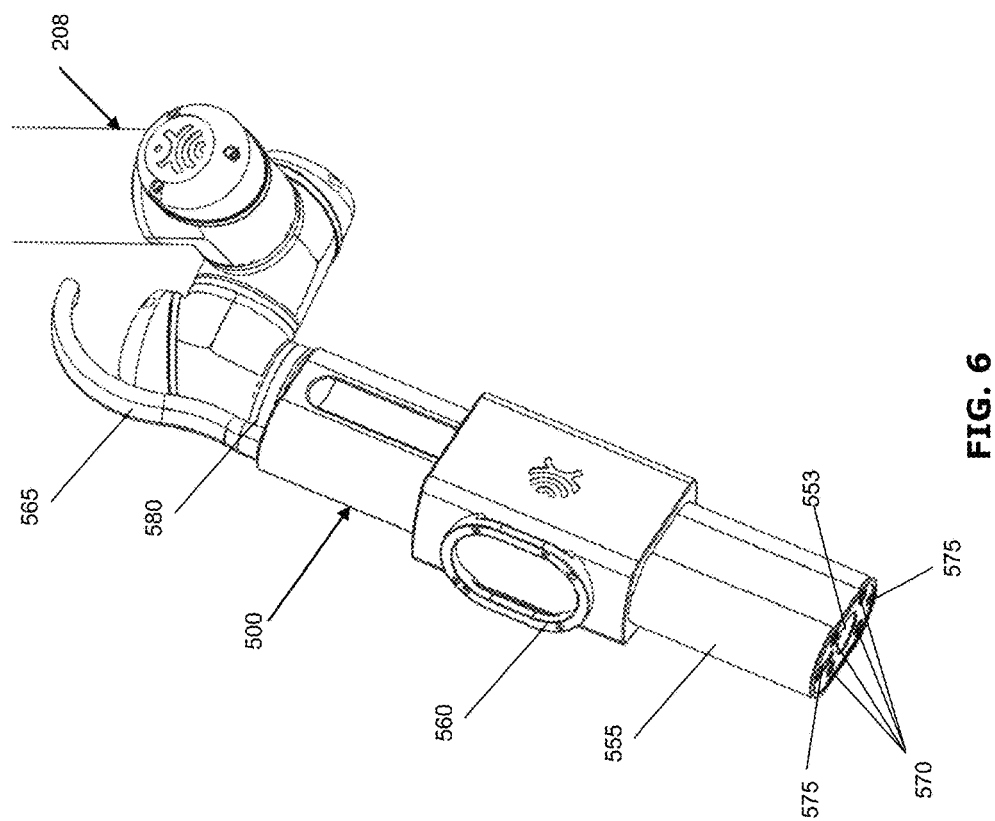
FIGS. 6 and 7 are different perspective views of an example optical imaging system.
Figure 7:
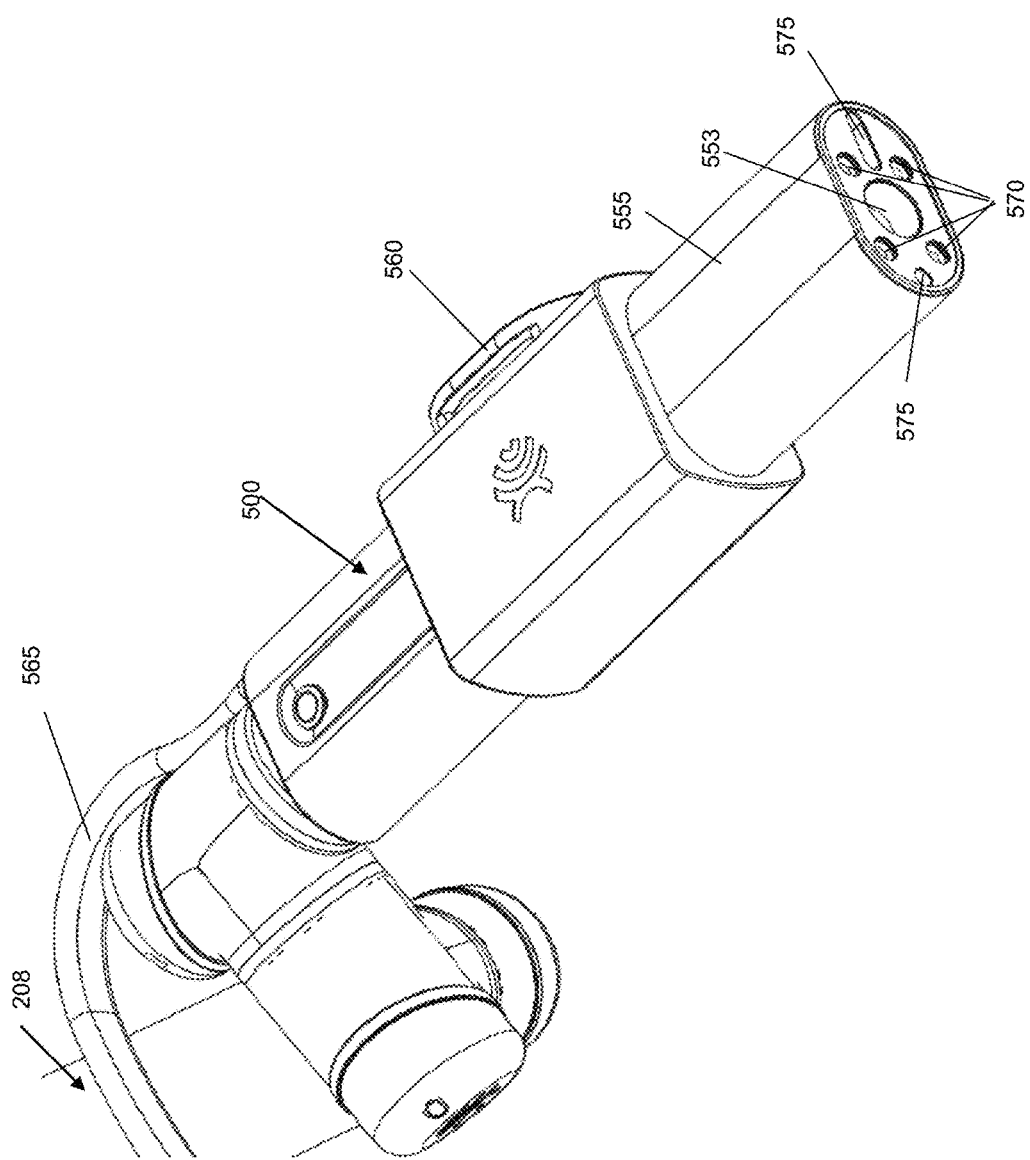

FIGS. 6 and 7 are perspective views of an example embodiment of the imaging system 500. In this example, the imaging system 500 is shown mounted to the positioning system 208 (e.g., a robotic arm) of a navigation system. The imaging system 500 is shown with a housing 555 that encloses the zoom and focus optics, the zoom and focus actuators, the camera, the controller and the 3D scanner, discussed further below with reference to FIG. 8. The housing is provided with a frame 560 on which trackable markers may be mounted, to enable tracking by the navigation system. The imaging system 500 communicates with the navigation system via a cable 565 (shown partially cut off). The distal end of the imaging system 500 is provided with light sources 570. The example shows four broad spectrum LEDs, however more or less light sources 570 may be used, of any suitable type. Although the light sources 570 are shown provided surrounding the aperture 553 of the imaging system 500, in other examples the light source(s) 570 may be located elsewhere on the imaging system 500. The distal end of the imaging system 500 may also include openings 575 for the cameras of the integrated 3D scanner. A support connector 580 for mounting the imaging system 500 to the positioning system 208 is also shown, as well as the frame 560 for mounting trackable markers.

Figure 8:
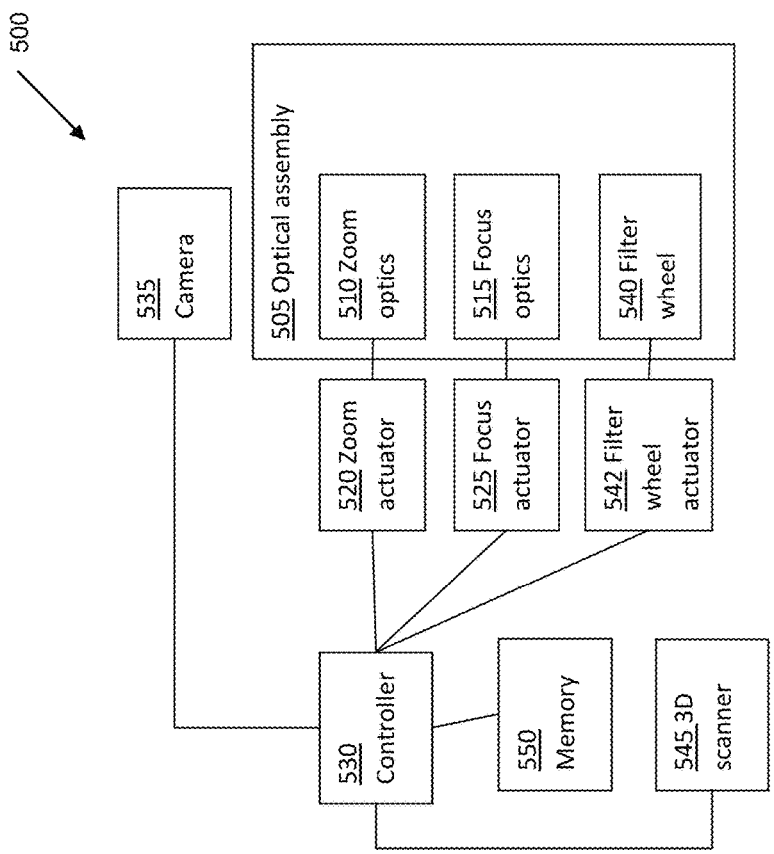
FIG. 8 is a block diagram of an example optical imaging system.

FIG. 8 is a block diagram showing components of an example imaging system 500, which may be a surgical microscope. The imaging system 500 may include an optical assembly 505 (also referred to as an optical train). The optical assembly 505 may include optics (e.g., lenses, optical fibers, etc.) for focusing and zooming on the viewing target. The optical assembly 505 may include zoom optics 510 (which may include one or more zoom lenses) and focus optics 515 (which may include one or more focus lenses). Each of the zoom optics 510 and focus optics 515 are independently moveable within the optical assembly, in order to adjust the zoom and focus, respectively. Where the zoom optics 510 and/or the focus optics 515 include more than one lens, each individual lens may be independently moveable. The optical assembly 505 may include an aperture (not shown), which may be adjustable.

The imaging system 500 may include a zoom actuator 520 and a focus actuator 525 for positioning the zoom optics 510 and the focus optics 515, respectively. The zoom actuator 520 and/or the focus actuator 525 may be an electric motor, or other types of actuators including, for example, pneumatic actuators, hydraulic actuators, shape-changing materials (e.g., piezoelectric materials or other smart materials) or engines, among other possibilities. In some examples, the zoom actuator 520 and/or the focus actuator 525 may be implemented using a stepper motor and string-pulley drive system, for example as described in US Pat. Pub. No. 2006/0187562, the entirety of which is hereby incorporated by reference.

Although the term "motorized" is used in the present disclosure, it should be understood that the use of this term does not limit the present disclosure to use of motors necessarily, but is intended to cover all suitable actuators, including motors. Although the zoom actuator 520 and the focus actuator 525 are shown outside of the optical assembly 505, in some examples the zoom actuator 520 and the focus actuator 525 may be part of or integrated with the optical assembly 505. The zoom actuator 520 and the focus actuator 525 may operate independently, to control positioning of the zoom optics 510 and the focus optics 515, respectively. The lens(es) of the zoom optics 510 and/or the focus optics 515 may be each mounted on a linear stage (e.g., a motion system that restricts an object to move in a single axis, which may include a linear guide and an actuator; or a conveyor system such as a conveyor belt mechanism) that is moved along a set of rails by the zoom actuator 520 and/or the focus actuator 525, respectively, to control positioning of the zoom optics 510 and/or the focus optics 515. The independent operation of the zoom actuator 520 and the focus actuator 525 may enable the zoom and focus to be adjusted independently. Thus, when an image is in focus, the zoom may be adjusted without requiring further adjustments to the focus optics 515 to produce a focused image.

Operation of the zoom actuator 520 and the focus actuator 525 may be controlled by a controller 530 (e.g., a microprocessor) of the imaging system 500. The controller 530 may receive control input (e.g., from an external system, such as an external processor or an input device). Where the imaging system 500 is used as part of the navigation system 205, the controller 530 may communicate with and receive control input from a processor of the navigation system 205. The control input may indicate a desired zoom and/or focus, and the controller 530 may in response control the zoom actuator 520 and/of focus actuator 525 to move the zoom optics 510 and/or the focus optics 515 accordingly to achieve the desired zoom and/or focus. In some examples, the zoom optics 510 and/or the focus optics 515 may be moved or actuated without the use of the zoom actuator 520 and/or the focus actuator 525. For example, the focus optics 515 may use electrically-tunable lenses or other deformable material that may be controlled directly by the controller 530.

By providing the controller 530, the zoom actuator 520 and the focus actuator 525 all as part of the imaging system 500, the imaging system 500 may enable an operator (e.g., a surgeon) to control zoom and/or focus during a medical procedure without having to manually adjust the zoom and/or focus optics 510, 515. For example, the operator may provide control input to the controller 530 verbally (e.g., via a voice recognition input system), by instructing an assistant to enter control input into an external input device (e.g., into a user interface provided by a workstation), using a foot pedal, or by other such means. In some examples, the controller 530 may carry out preset instructions to maintain the zoom and/or focus at preset values (e.g., to perform autofocusing) without requiring further control input during the medical procedure.

As mentioned above, an external processor (e.g., a processor of a workstation or the navigation system) in communication with the controller 530 may be used to provide control input to the controller 530. For example, the external processor may provide a graphical user interface via which the operator or an assistant may input instructions to control zoom and/or focus of the imaging system 500. The controller 530 may alternatively or additionally be in communication with an external input system (e.g., a voice recognition input system or a foot pedal).

The optical assembly 505 may also include one or more auxiliary optics such as a filter wheel 540 for selecting an optical filter for imaging. The filter wheel 540 may hold one or more optical filters, for example an optical filter for fluorescence imaging. The filter wheel 540 may be actuated by a filter wheel actuator 542, which may be controlled by the controller 530, to place a selected optical filter in the optical path.

The imaging system 500 may also include a camera 535 (e.g., a high-definition (HD) camera) that captures image data from the optical assembly. Operation of the camera may be controlled by the controller 530. The camera 535 may also output data to an external system (e.g., an external workstation or external output device) to view the captured image data. In some examples, the camera 535 may output data to the controller 530, which in turn transmits the data to an external system for viewing. By providing image data to an external system for viewing, the captured images may be viewed on a larger display and may be displayed together with other information relevant to the medical procedure, including navigational information (e.g., a wide-field view of the surgical site, navigation markers, 3D images, etc.). Providing the camera 535 with the imaging system 500 may help to improve the consistency of image quality among different medical centers.

Image data captured by the camera 535 may be displayed on a display together with a wide-field view of the surgical site, for example in a multiple-view user interface. The portion of the surgical site that is captured by the camera 535 may be visually indicated in the wide-field view of the surgical site.

The imaging system 500 may include a three-dimensional (3D) scanner 545 or 3D camera for obtaining 3D information of the viewing target. 3D information from the 3D scanner 545 may also be captured by the camera 535, or may be captured by the 3D scanner 545 itself. Operation of the 3D scanner 545 may be controlled by the controller 530, and the 3D scanner 545 may transmit data to the controller 530. In some examples, the 3D scanner 545 may itself transmit data to an external system (e.g., an external work station). 3D information from the 3D scanner 545 may be used to generate a 3D image of the viewing target (e.g., a 3D image of a target tumor to be resected). 3D information may also be useful in an augmented reality (AR) display provided by an external system. For example an AR display (e.g., provided via AR glasses) may, using information from a navigation system to register 3D information with optical images, overlay a 3D image of a target specimen on a real-time optical image (e.g., an optical image captured by the camera 535).

The controller 530 may be coupled to a memory 550. The memory 550 may be internal or external of the imaging system 500. Data received by the controller 530 (e.g., image data from the camera 535 and/or 3D data from the 3D scanner) may be stored in the memory 550. The memory 550 may also contain instructions to enable the controller to operate the zoom actuator 520 and the focus actuator 525. For example, the memory 550 may store instructions to enable the controller to control the actuators 520, 525 according to different control parameters, as discussed further below.

The imaging system 500 may communicate with an external system (e.g., a navigation system or a workstation) via wired or wireless communication. In some examples, the imaging system 500 may include a wireless transceiver (not shown) to enable wireless communication.

In some examples, the imaging system 500 may include a power source (e.g., a battery) or a connector to a power source (e.g., an AC adaptor). In some examples, the imaging system 500 may receive power via a connection to an external system (e.g., an external workstation or processor).

In some examples, the imaging system 500 may include a light source (not shown). In some examples, the light source may not itself generate light but rather direct light from another light generating component. For example, the light source may be an output of a fibre optics cable connected to another light generating component, which may be part of the imaging system 500 or external to the imaging system 500. The light source may be mounted near the aperture of the optical assembly, to direct light to the viewing target. Providing the light source with the imaging system 500 may help to improve the consistency of image quality among different medical centers. In some examples, the power or output of the light source may be controlled by the imaging system 500 (e.g., by the controller 530) or may be controlled by a system external to the imaging system 500 (e.g., by an external workstation or processor, such as a processor of a navigation system).

In some examples, the optical assembly 505, zoom actuator 520, focus actuator 525 and camera 535 may all be housed within a single housing of the imaging system 500. In some examples, the controller 530, memory 550, 3D scanner 545, wireless transceiver, power source and/or light source may also be housed within the housing.

In some examples, the imaging system 500 may also provide mechanisms to enable manual adjusting of the zoom and/or focus optics 510, 515, similarly to conventional systems. Such manual adjusting may be enabled in addition to motorized adjusting of zoom and focus. In some examples, such manual adjusting may be enabled in response to user selection of a "manual mode" on a user interface.

The imaging system 500 may be mountable on a moveable support structure, such as the positioning system (e.g., robotic arm) of a navigation system, a manually operated support arm, a ceiling mounted support, a moveable frame, or other such support structure. The imaging system 500 may be removably mounted on the moveable support structure. In some examples, the imaging system 500 may include a support connector (e.g., a mechanical coupling) to enable the imaging system 500 to be quickly and easily mounted or dismounted from the support structure. The support connector on the imaging system 500 may be configured to be suitable for connecting with a typical complementary connector on the support structure (e.g., as designed for typical end effectors). In some examples, the imaging system 500 may be mounted to the support structure together with other end effectors, or may be mounted to the support structure via another end effector.

When mounted, the imaging system 500 may be at a known fixed position and orientation relative to the support structure (e.g., by calibrating the position and orientation of the imaging system 500 after mounting). In this way, by determining the position and orientation of the support structure (e.g., using a navigation system or by tracking the movement of the support structure from a known starting point), the position and orientation of the imaging system 500 may also be determined. In some examples, the imaging system 500 may include a manual release button that, when actuated, enable the imaging system 500 to be manually positioned (e.g., without software control by the support structure).

In some examples, where the imaging system 500 is intended to be used in a navigation system environment, the imaging system 500 may include an array of trackable markers, which may be mounted on a frame on the imaging system 500) to enable the navigation system to track the position and orientation of the imaging system 500. Alternatively or additionally, the moveable support structure (e.g., a positioning system of the navigation system) on which the imaging system 500 is mounted may be tracked by the navigation system and the position and orientation of the imaging system 500 may be determined using the known position and orientation of the imaging system 500 relative to the moveable support structure.

The trackable markers may include passive reflective tracking spheres, active infrared (IR) markers, active light emitting diodes (LEDs), a graphical pattern, or a combination thereof. There may be at least three trackable markers provided on a frame to enable tracking of position and orientation. In some examples, there may be four passive reflective tracking spheres coupled to the frame. While some specific examples of the type and number of trackable markers have been given, any suitable trackable marker and configuration may be used, as appropriate.

Determination of the position and orientation of the imaging system 500 relative to the viewing target may be performed by a processor external to the imaging system 500 (e.g., a processor of the navigation system). Information about the position and orientation of the imaging system 500 may be used, together with a robotic positioning system, to maintain alignment of the imaging system 500 with the viewing target (e.g., to view down an access port during port-based surgery) throughout the medical procedure.

For example, the navigation system may track the position and orientation of the positioning system and/or the imaging system 500 either collectively or independently. Using this information as well as tracking of the access port, the navigation system may determine the desired joint positions for the positioning system so as to maneuver the imaging system 500 to the appropriate position and orientation to maintain alignment with the viewing target (e.g., the longitudinal axes of the imaging system 500 and the access port being aligned). This alignment may be maintained throughout the medical procedure automatically, without requiring explicit control input. In some examples, the operator may be able to manually move the positioning system and/or the imaging system 500 (e.g., after actuation of a manual release button). During such manual movement, the navigation system may continue to track the position and orientation of the positioning system and/or the imaging system 500. After completion of manual movement, the navigation system may (e.g., in response to user input, such as using a foot pedal, indicating that manual movement is complete) reposition and reorient the positioning system and the imaging system 500 to regain alignment with the access port.

The working distance may be determined by the controller 530 using information (e.g., received from the navigation system, from the positioning system or other external system) about the position and orientation of the imaging system 500 and/or the positioning system relative to the viewing target. In some examples, the working distance may be determined by the controller 530 using an infrared light (not shown) mounted on near the distal end of the imaging system 500.

In some examples, the mechanism for moving the zoom optics may be a stepper motor and string-pulley drive system. Using such a drive system, it may not be practical or possible to implement a gear ratio that is adequate for high precision and high accuracy in control, when a high zoom level is used. Backlash in the gearbox and insufficiency in the holding force may also result in movement of the optical image, causing image instability, which may also be variable with the orientation of the imaging system. The pulley drive mechanism may be sensitive to backlash, which may prevent or hinder use of the drive system for fine movement at a high zoom level. As well, there may be variation in friction along the rail on which the zoom optics are moved.

Figure 9:
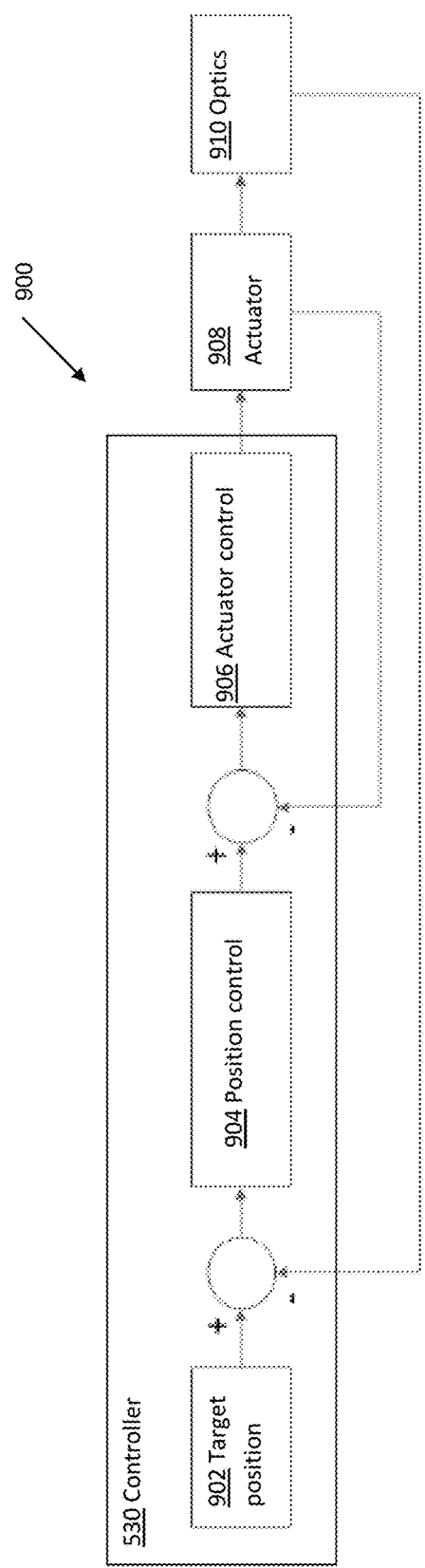
FIG. 9 is a block diagram illustrating an example control loop for an example optical imaging system.

FIG. 9 illustrates an example control loop 900 that may be used by the controller 530 to control the zoom optics 510 and/or the focus optics 515. For the purpose of generalization, FIG. 9 illustrates control for general optics 910 that are positioned by a general actuator 908. It should be understood that the actuator 908 may be the zoom actuator 520 and/or the focus actuator 525, and the optics 910 may be the zoom optics 510 and/or the focus optics 515. A single instance of the control loop 900 may be used to control a single set of optics 910. Thus, there may be multiple instances of the control loop 900. For example, there may be three such control loops 900 implemented by the controller 530—one control loop 900 to control the focus optics 515, and two control loops 900 to control two zoom optics 510. The control loops 900 may be implemented using a master-slave configuration, in which the controller 530 includes a master controller and each set of optics 910 is controlled by a respective slave controller.

A single instance of the control loop 900 is now described. The target position 902 (e.g., received as control input into the master controller) is inputted into the position control 904 (which may be implemented by the master controller, where a master-slave configuration is used), which implements a proportional-integral-derivative (PID) control loop, represented by the transfer function (in the Laplace domain) $Kp+Ki/s+Kd*s$, where s is the complex frequency and the control terms are Kp (proportional), Ki (integral) and Kd (derivative). The actual monitored position of the optics 910 is a negative feedback to the position control 904. The output of the position control 904 is inputted to the actuator control 906 (which may be implemented by a slave controller, where a master-slave configuration is used), which controls the current of the actuator 908 (e.g., brushless DC (BLDC) motor). The actuator control 906 implements a proportional-integral (PI) control loop, represented by the transfer function (in the Laplace domain) $Kp+Ki/s$. The actual current of the actuator 908 is a negative feedback to the actuator control 906.

In some conventional surgical microscopes, at steady state the conventional system sometimes exhibits a state of instability, resulting in oscillations of the image. This may be due to variations in friction and/or stiction in the physical movement of the optics, and may also be due to backlash in the gearing of the actuation motor. Although such instability may be mitigated by using less aggressive position control parameters, the trade-off is a poorer step response time, which may not satisfy user requirements.

In the disclosed imaging system, instead of using a single set of control parameters, the controller 530 controls each instance of the control loop 900 according to two sets of control parameters, in this case two sets of PID parameters thus implementing a dual-PID control. Such a configuration may help to mitigate the jitter and instability challenges discussed above. PID controls are typically used to control systems with a defined input (in this case a target position 902) and an output (in this case the actual position of the optics 910) that can be monitored.

Figure 10:
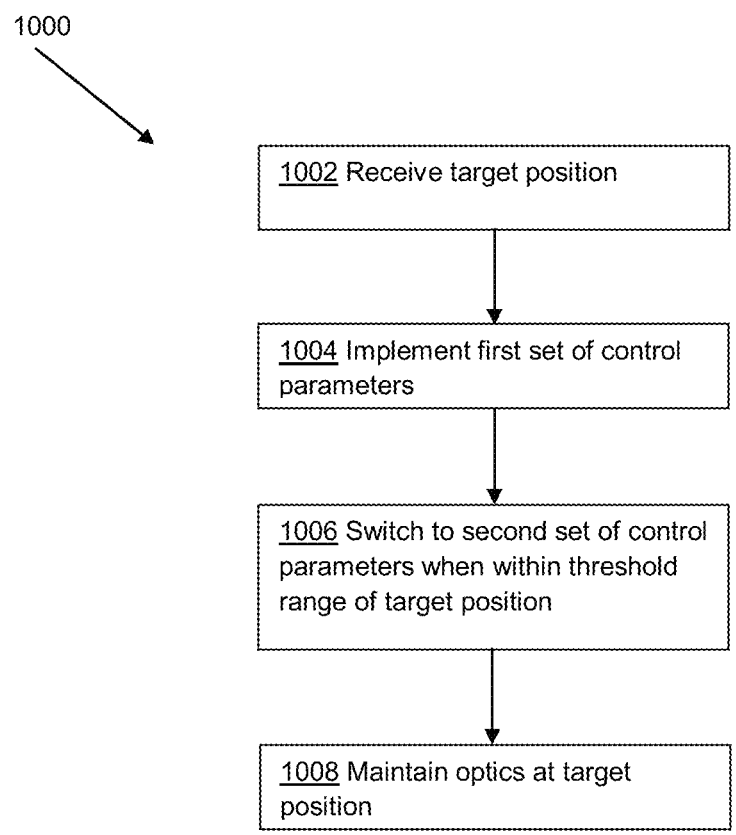
FIG. 10 is a flowchart illustrating an example method of controlling an optical imaging system.

FIG. 10 is a flowchart illustrating an example method 1000 for controlling the optics 910, according to two sets of control parameters. The method 1000 may be performed by the controller 530 to control each set of optics (e.g., each set of focus optics and zoom optics) independently. Each set of optics may have their own respective first and second sets of control parameters.

At 1002, a new target position 902 is received into the control loop 900, to change the position of the optics 910 from the current steady state.

At 1004, the controller 530 implements a first set of control parameters, which may be referred to as coarse control parameters K(a). The coarse control parameters K(a) are designed to be more aggressive, to move the optics 910 more quickly. The position of the optics 910 may be detected by a sensor (e.g., opto-electrical sensor) in the imaging system 500, or otherwise tracked or determined by the controller 530.

At 1006, when the optics 910 are within a tolerance or threshold range (e.g., within 10 μm) of the target position 902 (e.g., for at least a threshold amount of time), the controller 530 switches to a second set of control parameters, which may be referred to as fine control parameters K(c). The fine control parameters K(c) are designed to be more conservative, to move the optics 910 more carefully and slowly. The second set of control parameters K(c) may have Kp(c) and Kd(c) control terms similar to the Kp(a) and Kd(a) control terms of the first set of control parameters K(a), but may have a smaller Ki(c) control term (e.g., by a factor of about 2 to 3) than the Ki(a) control term of the first set of control parameters K(a). By using a smaller Ki(c) term, the long-term effect of small deviations in position is reduced.

In some examples, the controller 530 may also switch from the first set of control parameters K(a) to the second set of control parameters K(c) upon expiry of a preset timer, regardless of the position of the optics 910. This may be a fail-safe mechanism.

At 1008, when the optics 910 reaches the target position 902, the controller 530 maintains the optics 910 at steady state at the target position 902, using the second set of control parameters K(c), until a new target position 902 is received.

In some examples, the controller 530 may also implement a clamp on the integrated error sum to prevent integrator windup.

Using the example method 1000, the imaging system 500 may achieve a fast step response time (e.g., negligible lag between user input and change in focus and/or zoom) while achieving a position accuracy for the optics 910 of 10 μm or less at steady state (i.e., when holding a desired focus and/or zoom).

The control terms for the first and second set of control parameters K(a), K(c) may be individually adjusted or otherwise defined for each individual imaging system 500 (e.g., at the manufacturing stage), in order to achieve the desired level of stability and in order to account for individual variations (e.g., variations in rail friction for each imaging system).

Figure 11:
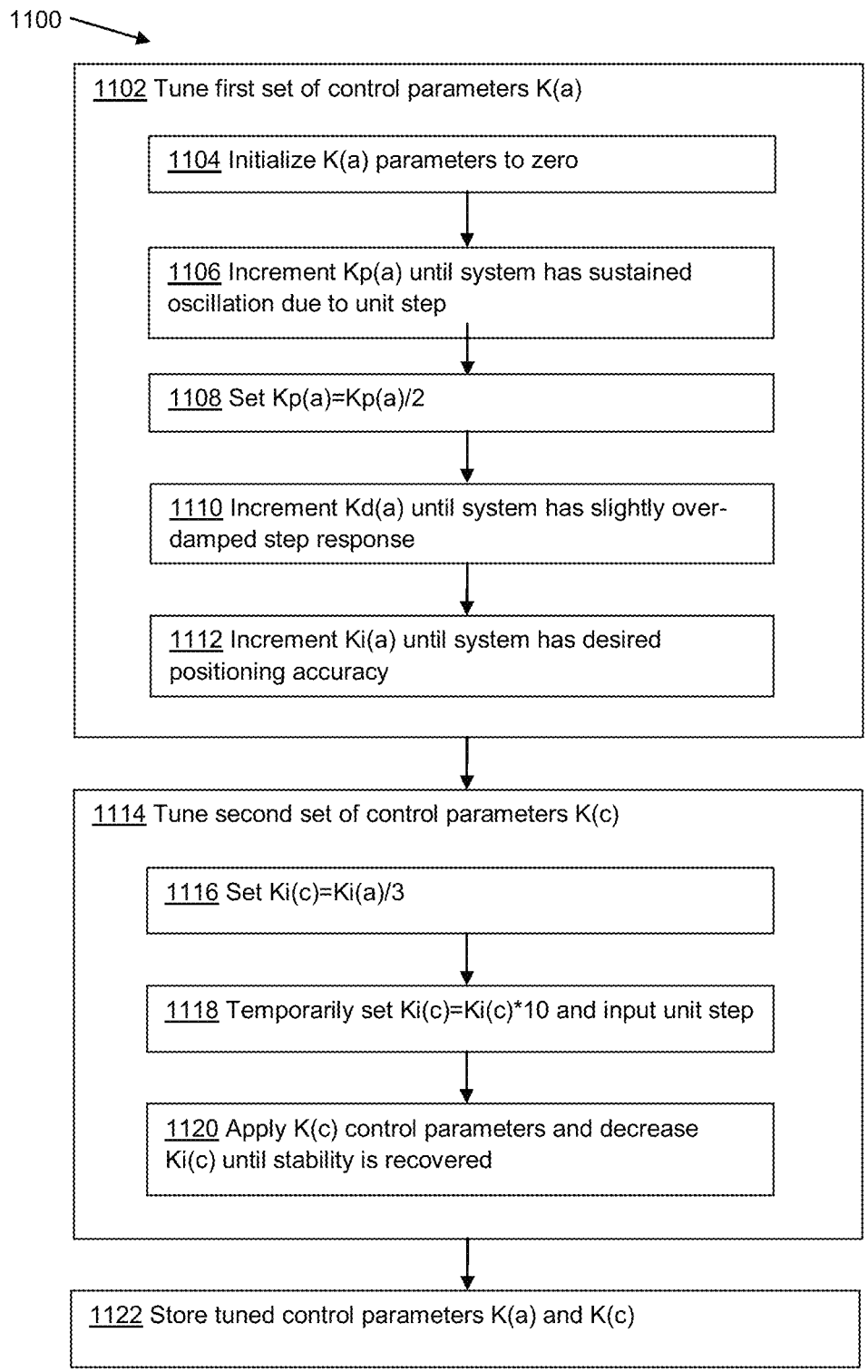
FIG. 11 is a flowchart illustrating an example method of setting control parameters for an optical imaging system.

The control parameters K(a), K(c) may be tuned using any suitable techniques, for example using a modified version of the heuristic Ziegler and Nichols method. FIG. 11 is a flowchart illustrating an example tuning method 1100 for the control parameters K(a), K(c). The method 1100 may be performed by the controller 530 of the imaging system 500, or by an external controller.

Tuning of the first set of control parameters K(a), which is the more aggressive set of parameters, is performed first at 1102.

At 1104, all control terms of K(a) are initiated with zero gains.

At 1106, Kp(a) is incremented until the system exhibits a sustained oscillation due to a unit step.

At 1108, set Kp(a)=Kp(a)/2. In some examples, a factor other than two may be used, as appropriate.

At 1110, Kd(a) is incremented until the system achieves a slightly over-damped step response. The typical ratio of Kd(a):Kp(a) that achieved this result has been found to be about 4:1, for the example imaging system driven using a pulley system as described above.

At 1112, Ki(a) is incremented until the system achieves the desired positioning accuracy. The ratio of Ki(a) to the other control terms was found to vary among individual systems.

Tuning of the second set of control parameters K(c), which is the more conservative set of parameters, is performed next at 1114, based on the first set of control parameters K(a).

At 1116, set Ki(c)=Ki(a)/3. In some examples, instead of a reduction by a factor of three, a reduction by another factor, for example 2 or some other amount in a similar range, may be used.

At 1118, temporarily set Ki(c)=Ki(c)*10 and input a unit step to induce system instability.

At 1120, apply the control parameters K(c). If the system does not return to a stable state, Ki(c) is decreased (e.g., by intervals of 0.1) until stability is recovered.

At 1122, the tuned control parameters K(a) and K(c) are stored in memory, to be accessed by the controller 530 when needed (e.g., for the method 1000).

The method 1100 may be performed for each individual imaging system 500, and may be performed by the manufacturer. The method 1100 may be performed for each set of optics (e.g., each set of focus optics and zoom optics) to obtain control parameters for each set of optics independently. The method 1100 may also be performed any time during the lifetime of the imaging system 500, for example to adjust the control parameters for greater stability requirements and/or to adjust the control parameters for changes in the physical properties of the imaging system 500 (e.g., changes in friction of the actuator, due to wear and tear over the lifetime of the imaging system 500).

Although two sets of control parameters, K(a) and K(c), have been discussed, in some examples there may be more than two sets of control parameters. For example, there could be multiple sets of control parameters that can be selectively used for different operation conditions. In some examples, the control parameters may be a function of one or more other variables or parameters. For example, the control loop 900 may use a set of control parameters that is a function of the zoom level (e.g., the control parameters may be less aggressive at a higher zoom level and more aggressive at a lower zoom level).

Figure 12:
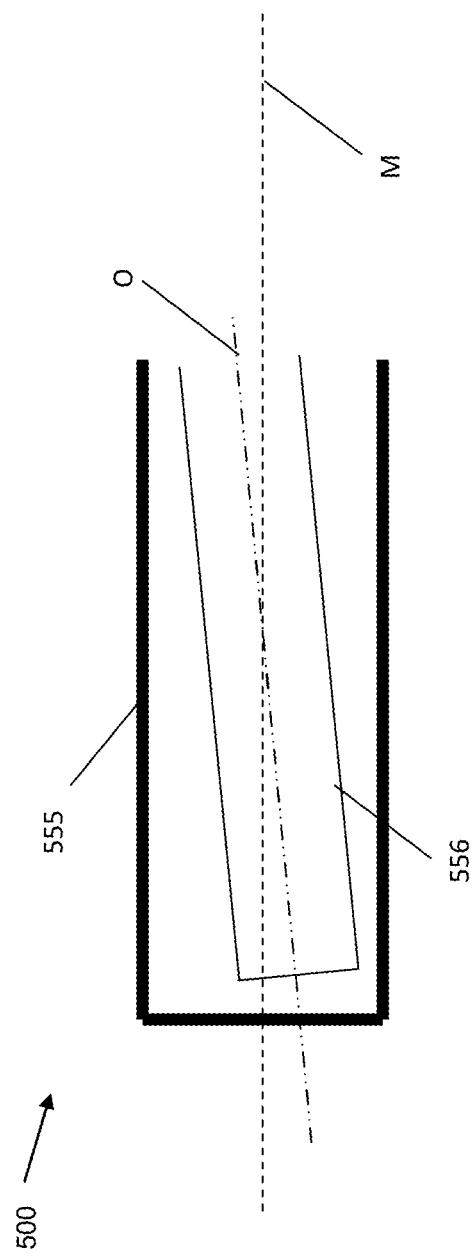
FIG. 12 is a diagram illustrating an exaggerated misalignment of the optical axis in an optical imaging system.

In some examples, there may be a misalignment between the mechanical axis of the imaging system and its optical axis. An example of such a misalignment is illustrated in FIG. 12, with dimensions exaggerated for clarity. FIG. 12 illustrates an imaging system 500 in which the housing 555 has a longitudinal axis defining a mechanical axis M of the imaging system. The optical train 556 of the imaging system 500 has an optical axis O, which is the axis for capturing an optical image. Although shown as an exaggerated misalignment in one degree of freedom, typically the misalignment is small (e.g., about 0.15° to about 0.25°, in some examples no more than a maximum of 4°) and may be in more than one degree of freedom (e.g., may be translational and/or rotational along and/or around the x, y and/or z-axes). In typical applications, such misalignment may not be noticeable. However, in surgical microscope applications, due to the high zoom level required together with the relatively large working distance, even a misalignment of 0.1° may be unacceptable.

As described above, the imaging system 500 may be supported by a positioning system, such as a robotic arm, and the position and orientation of the imaging system 500 may be changed by moving the positioning system. The position and orientation of the imaging system 500 may be tracked by a tracking system that tracks tracking markers coupled to the housing 555 of the imaging system 500 and/or tracking markers coupled to the robotic arm. The positioning of the imaging system 500 may be based on the assumption that the optical axis O is aligned with the mechanical axis M. For example, to increase or decrease the working distance of the imaging system 500, the imaging system 500 may be moved along the mechanical axis M. However, if there is misalignment between the optical axis O and the mechanical axis M, then when the imaging system 500 is moved along the mechanical axis M, the center point of the captured image with shift, resulting in a shift in the field-of-view (FOV) of the captured image. This shift is undesirable and unexpected for the surgeon. This FOV error may be significant when using the high zoom level and long working distance required for surgical microscopes during a surgical procedure.

Table 1 below illustrates the FOV error (as percentage of FOV) that may arise for example angular misalignment that may be found in typical imaging systems, at various working distances and zoom levels that may be used during a surgical procedure.

| Working distance (mm) | Zoom (x) | Angular misalignment | | | |
|---|---|---|---|---|---|
| | | 4° | 0.15° | 0.26° | 0.20° |
| 200 | 1 | 17% | <1% | 1% | <1% |
| 650 | 1 | 22% | <1% | 1% | 1% |
| 200 | 12.5 | 215% | 1% | 14% | 10% |
| 650 | 12.5 | 274% | 10% | 18% | 14% |

Figure 13:
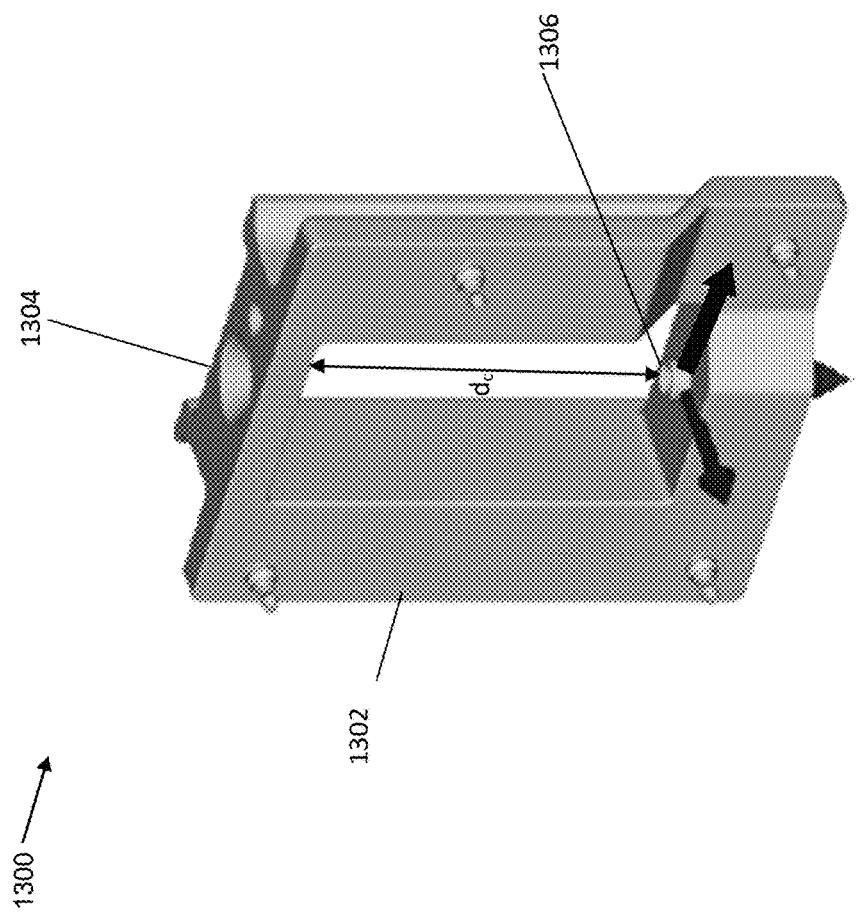
FIG. 13 is a perspective view of an example calibration apparatus for calibrating the optical axis of an optical imaging system.
Figure 14:
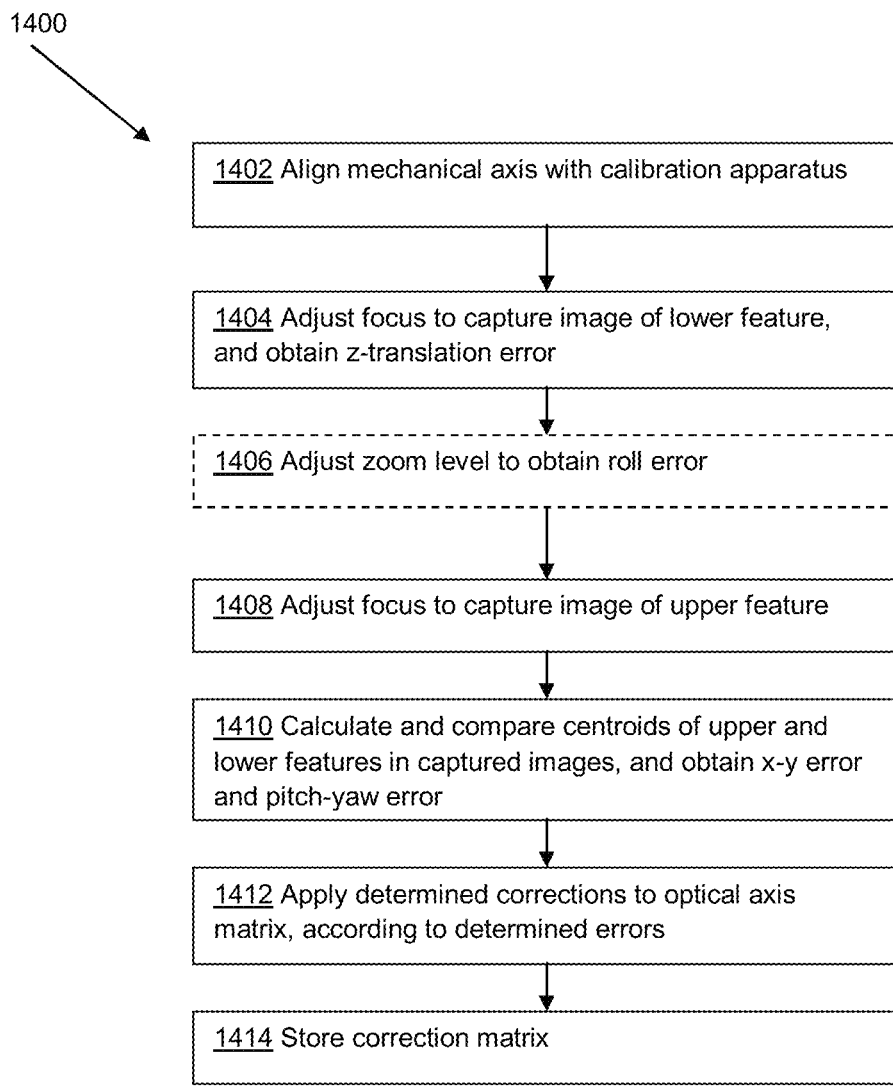
FIG. 14 is a flowchart illustrating an example method of calibration for an optical imaging system.

To compensate for such misalignment, a calibration of the optical axis may be performed. Using the example calibration technique described below, a transformation may be calculated, which may be used to compensate for misalignment of the optical axis, including translational as well as rotational misalignment in six degrees of freedom. An example of a calibration apparatus 1300 for calibrating the optical axis is shown in FIG. 13. The calibration apparatus 1300 may be used for performing the example calibration method 1400 illustrated in FIG. 14. FIGS. 13 and 14 will be described together.

Calibration of the optical axis may be performed using the tracking system together with video processing of the captured image. The calibration may be performed using the processor of the navigation system 205, for example, as part of setting up of the navigation system 205 prior to the start of a medical procedure. In some examples, calibration of the optical axis may be performed by the manufacturer. The optical axis may be calibrated at the start of every medical procedure, during the medical procedure, or only at defined time intervals (e.g., weekly), for example.

The calibration apparatus 1300 has a body 1302 in which is defined an upper feature (in this example an upper bore hole 1304) and a lower feature (in this example a divot 1306) that are aligned longitudinally and separated by a known distance $d_c$.

At 1402, the optical system 500 is positioned to have its mechanical axis aligned with the longitudinal axis of the calibration apparatus 1300, and at a maximum working distance and maximum zoom level from the lower divot 1306. The optical system 500 is thus positioned to capture an image of the lower divot 1306.

At 1404, the focus of the imaging system 500 is adjusted to bring the lower feature (e.g. divot) 1306 into focus. This focus adjustment is the z-translation error. A first image of the lower feature (e.g. divot) 1306 is captured.

At 1406, optionally, the zoom level of the imaging system 500 may be decreased to perform roll error calibration. In some examples, it may not be necessary to correct for roll error, because typically the imaging system 500 may be manufactured such that the roll error is already small enough and does not require correction. If correction of roll error is required, the roll error may be calculated by measuring the angular amount by which a horizontal or vertical line in the image deviates from the actual horizontal or vertical of the image.

At 1408, the focus of the imaging system 500 is adjusted by the known distance $d_c$, to capture a second image of the upper feature (e.g. bore hole) 1304.

At 1410, the processor (e.g., processor of the navigation system 205, an onboard processor of the imaging system 500, or another external processor) determines the centroids of the upper feature (e.g. bore hole) 1304 and lower feature (e.g. divot) 1306 captured in the first and second images. The x-y distance from the calculated centroid of the lower feature (e.g. divot) 1306 and the actual center of the image is the x-y translation error. The x-y distance between the calculated centroid of the lower feature (e.g. divot) 1306 and the calculated centroid of the upper feature (e.g. bore hole) is the pitch-yaw error. An example calculation is shown below:

$$\theta_x = \tan^{-1}\left(\frac{x_{shift} * \frac{mm}{pixel}}{d_c}\right)$$

where $x_{shift}$ is the x-axis offset between the calculated centroids, mm/pixel is the known ratio of actual distance (mm) to each pixel of the image, $d_c$ is the known distance between the bore hole 1304 and divot 1306, and $\theta_x$ is the angular error.

At 1412, the determined errors are used to apply corrections to the optical axis matrix, to generate the correction terms for a correction matrix.

At 1414, the correction matrix is stored (e.g., by the processor that performed 1410). The correction matrix may thus be a transformation between the mechanical axis frame of reference and the optical axis frame of reference. Using the correction matrix, a desired increase or decrease of the working distance along the optical axis may be transformed to the necessary change in x/y/z and pitch/yaw/roll of the positioning system along the mechanical axis.

When a control input is received to move to a desired working distance, the processor (e.g., controller of the navigation system) may retrieve the correction matrix from memory and apply the correction matrix to transform the working distance to the mechanical axis frame of reference. The positioning system may then be controlled according to the transformed position and orientation.

In some examples, the calibration method 1400 may be repeated one or more times, to achieve a desired amount of correction (e.g., <0.1° misalignment). In some examples, the calibration apparatus 1300 may have other calibration points that may be used by the user to manually verify accuracy of the calibration.

Other calibration apparatuses may be used. For example, a different calibration target may use tracking markers for as calibration targets, or a crosshair instead of using upper and lower features (e.g. bore hole and divot, respectively).

In some examples, the imaging system 500 may include one or more selectable optical filters. For example, as shown in FIG. 8, the imaging system 500 may include a filter wheel 540 holding one or more optical filters. The filter wheel 540 may be driven by a filter wheel actuator 542, for example a stepper system that may be controlled by the controller 530 using an open-loop control. The filter wheel 540 may be positioned to place a selected optical filter in the optical path. One of the optical filters may enable the imaging system 500 to capture images in a fluorescence mode. Different optical filters may have different coatings that alter the optical path, for example due to refraction of light as light enters and exits the optical filter. An example of this is illustrated in FIG. 15.

Figure 15:
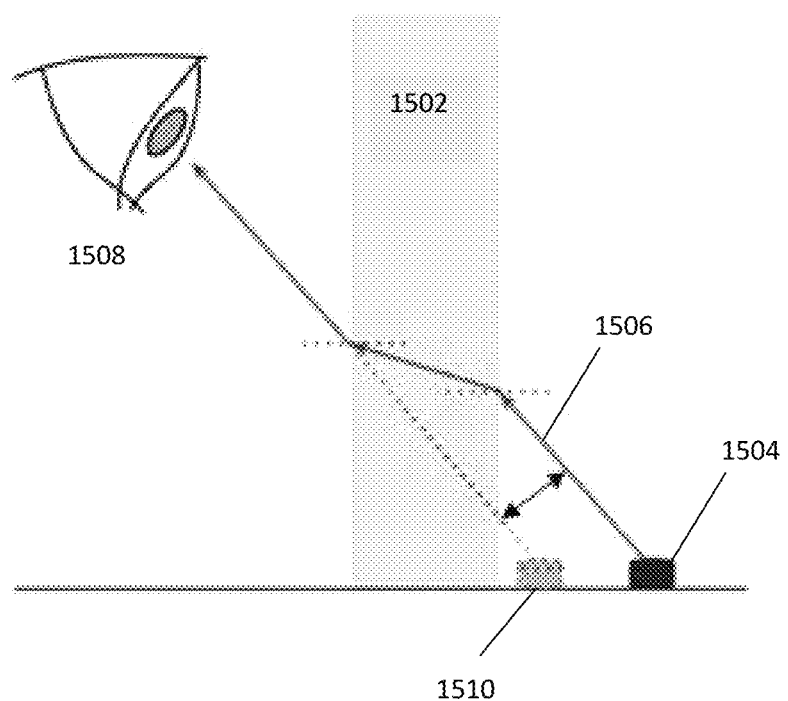
FIG. 15 is a diagram illustrating the shift in optical path caused by an optical filter.

FIG. 15 illustrates the shift in optical path caused by an optical filter 1502. Light from a target 1504 is refracted at each side of the optical filter 1502 (e.g., due to the coating on the optical filter 1502), such that the optical path 1506 is shifted. When the light is observed by a viewer 1508 (represented here as a human eye, but could be any light sensor, including any sensor or camera of the imaging system 500), the target 1504 is perceived to be at a position 1510 that is laterally shifted relative to the actual position of the target 1504. For the imaging system 500, this causes a shift in focal point which, if not compensated, requires the focus to be manually adjusted each time the optical filter 1502 is added, changed or removed, which can be burdensome and time-consuming.

In some examples, changes in temperature may also cause shift in the focal point, for example due to thermal characteristics of the optics. At a first temperature (e.g., 15° C.), the focus optics may be positioned at a first position x1 to focus on an object at a distance of 25 cm, and positioned at a second position x2 to focus on an object at a distance of 35 cm; at a different second temperature (e.g., 30° C.), the focus optics may need to be positioned at a third position x1+Δx1 to focus on an object at a distance of 25 cm, and need to be positioned at a fourth position x2+Δx2 to focus on an object at a distance of 35 cm.

The optical filter-related and temperature-related shifts of the focal point may be considered negligible or within acceptable tolerance in most optical applications. However, for a surgical microscope, operating at high zoom level and long working distance, even small shifts (e.g., on the order of 50 μm) may be noticeable and may cause unwanted disruption to the medical procedure. It may be necessary for the surgeon to interrupt the procedure to refocus the image, to ensure accuracy and precision of the procedure. This can be time-consuming and burdensome.

In some examples, the imaging system 500 may automatically compensate for such optical filter-related and temperature-related shifts. The optical properties of the imaging system 500 may be calibrated (e.g., during manufacturing, or at regular calibrations sessions) by empirical testing and/or simulations to determine the offset or shift caused by changes in temperature and/or changes in optical filter. In some cases, this offset may be represented by a polynomial (e.g., representing optical offset as a function of temperature). The offset may be specific to each individual imaging system 500 (e.g., dependent on specific optical design and the optical filters used). The offset determined by this calibration may be stored in a look-up table and/or reference polynomial (e.g., in a memory internal to the imaging system 500) and may be retrieved by the controller 530 of the imaging system 500 to perform compensation.

Figure 16:
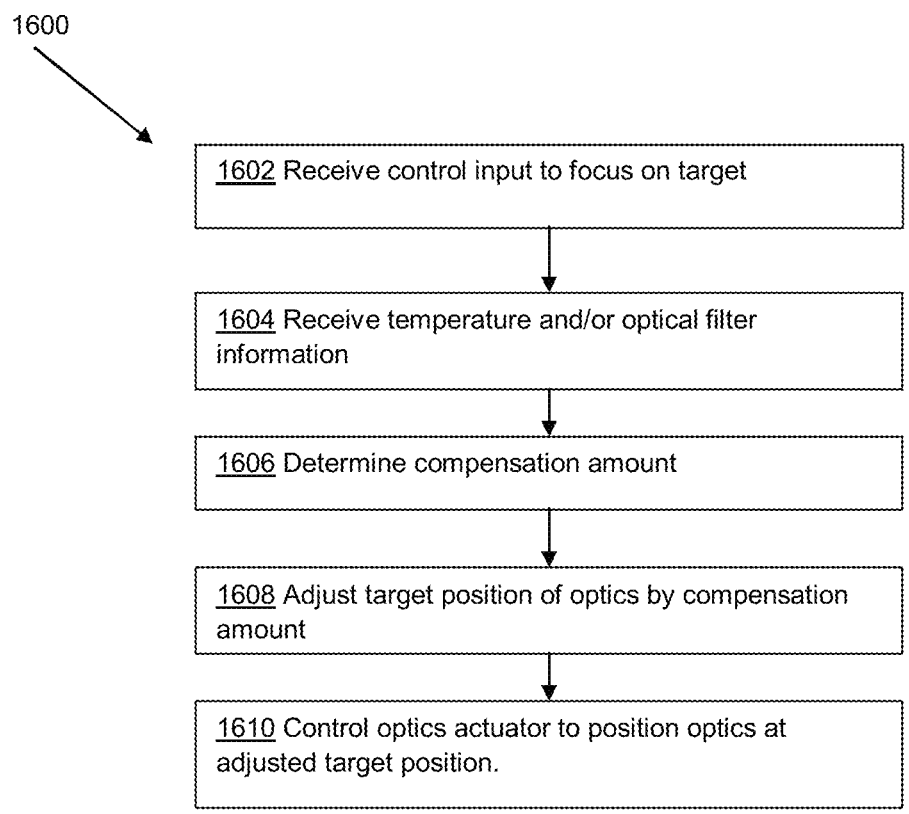
FIG. 16 is a flowchart illustrating an example method of compensating for temperature-related or optical filter-related shifts in an optical imaging system.

FIG. 16 is a flowchart illustrating an example method 1600 that may be performed by the controller 530 of the imaging system 500 to compensate for temperature-related and/or optical filter-related shifts.

At 1602, the controller 530 may receive a control input to focus on a target at a certain distance. For example, the controller 530 may receive control input from the navigation system 205 to focus on a target selected by a tracked pointing tool (e.g., as described in PCT/CA2015/050948, the entirety of which is hereby incorporated by reference).

At 1604, the controller 530 receives information from a temperature sensor (which may be internal to the imaging system 500) indicating the surrounding temperature of the optical assembly (or more specifically the optics). The controller 530 also receives information or determines if there is an optical filter being used and the type of optical filter being used.

At 1606, the controller 530 determines compensation amount by which the position of the optics (e.g., focus optics) should be adjusted to compensate for temperature-related and/or optical. The compensation amount may be determined by retrieving calibration data from a look-up table and/or by calculating using a reference polynomial.

At 1608, the controller 530 adjusts the target position of the optics by the compensation amount.

At 1610, the controller 530 controls the optics actuator (e.g., using the dual-PID control described above) to position the optics at the adjusted target position.

Although described above with respect to compensating for shifts in focal points by adjusting the position of the focus optics, a similar calibration and compensation may be carried out to compensate for optical filter-related and/or temperature-related shifts in the zoom optics, or other optics of the imaging system 500.

The example methods 1000, 1100, 1400, 1600 described above may be entirely performed by the controller of the imaging system, or may be partly performed by the controller and partly performed by an external system. For example, one or more of: determining the position/orientation of the imaging system, determining the position/orientation of the imaging target or medical instrument, determining the working distance, or determining the desired position of the focus optics may be performed by one or more external systems. The controller of the imaging system may simply receive commands, from the external system(s) to position the focus optics at the desired position, or the controller of the imaging system may determine the desired position of the focus optics after receiving the calculated working distance from the external system(s).

In various examples disclosed herein, methods, apparatuses and systems are described which may help to address the intensive optical requirements of a large variable focal distance and large variable zoom distance, for a compact, arm-mounted imaging system, such as a surgical microscope. Such an imaging system provides specific challenges in controlling the accuracy of the position of the optics. Conventional mechanical systems (e.g., pulley system) for most imaging systems may be controlled using a single set of control parameters, since the positioning errors and/or jitter are typically no more than on the order of micrometers, which is typically acceptable for most applications. However, in surgical microscopes, positioning errors and/or jitter on the order of micrometers are not acceptable. Hence, the need for more precise and accurate control, which is addressed by examples disclosed herein, is unique to the surgical microscope application.

The need for optical axis calibration is also unique to the surgical microscope application because the high magnification of the tracked imaging system leads to the manifestation of this error. At lower zoom levels, the optical axis misalignment is not noticeable.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read only memory (ROM), volatile random access memory (RAM), non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as any suitable programming or scripting language. Accordingly, the program code may be written in C, C++, J++, or any other suitable programming language and may comprise modules or classes, as is known to those skilled in programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A surgical microscope for capturing a high optical zoom image of a target during a surgical procedure, the surgical microscope comprising:
   an optical assembly including at least one moveable optics;
   an actuator for positioning the moveable optics, the actuator including a pulley system for moving the optics along a set of rails;
   a sensor for detecting the position of the moveable optics;
   a controller for controlling the actuator in response to received control input; and
   a camera for capturing the image of the target from the optical assembly; wherein the controller is configured to:
   receive control input indicating a target position for the moveable optics;
   control the actuator to position the moveable optics towards the target position, the actuator being controlled according to a first set of control parameters;
   upon receiving signals from the sensor indicating that the moveable optics is within a threshold range of the target position, switch to a second set of control parameters for controlling the actuator; and
   control the actuator to maintain the moveable optics at the target position at steady state;
   the first and second sets of control parameters being, respectively, first and second sets of proportional (P), integral (I) and derivative (D) terms for dual-PID control of the actuator.

2. The surgical microscope of claim 1 wherein the moveable optics includes moveable zoom optics and moveable focus optics, wherein the surgical microscope comprises at least two actuators for positioning the moveable optics, the at least two actuators including a zoom actuator for positioning the zoom optics and a focus actuator for positioning the focus optics, wherein the first set of control parameters include a first set of zoom control parameters and a first set of focus control parameters and the second set of control parameters include a second set of zoom control parameters and a second set of focus control parameters, and wherein the controller controls the zoom actuator and focus actuator independently according to the first and second sets of zoom control parameters and the first and second sets of focus control parameters.

3. The surgical microscope of claim 1 wherein the second set of control parameters has an I term smaller than the I term of the first set of control parameters by a factor in the range of about 2 to 3.

4. The surgical microscope of claim 1 further comprising a filter wheel, the filter wheel being positionable by a filter wheel actuator to position a selectable optical filter in an optical path of the optics.

5. The surgical microscope of claim 1 wherein use of a selectable optical filter causes a shift in an optical path in the optical assembly, and wherein the controller is further configured to determine a compensation amount to adjust the target position for the moveable optics, to compensate for the shift, and to adjust the target position accordingly.

6. The surgical microscope of claim 1 further comprising a temperature sensor, wherein the controller is further configured to determine a compensation amount to adjust the target position for the moveable optics, to compensate for temperature-dependent shift in an optical path of the optics, and to adjust the target position accordingly.

7. A method for controlling a surgical microscope for capturing a high optical zoom image, the method comprising:
   receiving control input indicating a target position for a moveable optics of the surgical microscope;
   controlling an actuator of the moveable optics to position the moveable optics towards the target position, the actuator being controlled according to a first set of control parameters, the actuator including a pulley system for moving the optics along a set of rails;
   upon receiving signals from a position sensor indicating that the moveable optics is within a threshold range of the target position, switching to a second set of control parameters for controlling the actuator; and
   controlling the actuator to maintain the moveable optics at the target position at steady state;

the first and second sets of control parameters being, respectively, first and second sets of proportional (P), integral (I) and derivative (D) terms for dual-PID control of the actuator.

8. The method of claim 6 wherein the moveable optics includes moveable zoom optics and moveable focus optics, wherein there are at least two actuators of the moveable optics, the at least two actuators including a zoom actuator for positioning the zoom optics and a focus actuator for positioning the focus optics, and wherein the first set of control parameters include a first set of zoom control parameters and a first set of focus control parameters and the second set of control parameters include a second set of zoom control parameters and a second set of focus control parameters, the method further comprising:

controlling the zoom actuator and focus actuator independently according to the first and second sets of zoom control parameters and the first and second sets of focus control parameters.

9. The method of claim 6 wherein the second set of control parameters has an I term smaller than the I term of the first set of control parameters by a factor in the range of about 2 to 3.

10. The method of claim 6, further comprising:

when a optical filter is positioned in an optical path of the optics, determining a compensation amount to adjust the target position for the moveable optics, to compensate for a shift in the optical path caused by the optical filter; and adjusting the target position accordingly.

11. The method of claim 6, further comprising:

receiving information from a temperature sensor indicating a surrounding temperature of the optics;

determining a compensation amount to adjust the target position for the moveable optics, to compensate for a temperature-dependent shift in an optical path of the optics; and adjusting the target position accordingly.

\* \* \* \* \*